United States Patent [19]

Saute

[11] Patent Number: 5,626,155

[45] Date of Patent: May 6, 1997

[54] METHOD OF CREATING FRAGRANCES IN SITU

[76] Inventor: Robert E. Saute, 10236 Mossy Rock Cir., Los Angeles, Calif. 90077

[21] Appl. No.: 391,727

[22] Filed: Feb. 21, 1995

Related U.S. Application Data

[63] Continuation of Ser. No. 139,570, Oct. 21, 1993, abandoned.

[51] Int. Cl.$^6$ ................................................. A45D 34/00
[52] U.S. Cl. ........................ 132/200; 434/377; 132/320
[58] Field of Search ........................ 434/377; 132/200, 132/320, 286, 294, 297, 317, 318; 206/232, 581, 823; 512/4; 422/4, 5

[56] References Cited

U.S. PATENT DOCUMENTS

| | | | |
|---|---|---|---|
| 1,546,302 | 7/1925 | Mehigan | 434/377 |
| 2,822,082 | 2/1958 | Breckwoldt et al. | 132/200 |
| 5,031,764 | 7/1991 | Meador et al. | 206/232 |
| 5,178,839 | 1/1993 | Spector | 434/377 |

*Primary Examiner*—Todd E. Manahan
*Attorney, Agent, or Firm*—Kenneth J. Hovet

[57] ABSTRACT

A method of producing a custom fragrance is provided comprising the steps of selecting a series of basic scents. The scents are incorporated into a semi-solid or solid vehicle to produce a scented product. With the semi-solid vehicle the product will be in the form of a viscous cream, gel or ointment contained in a squeeze tube, jar or the like. The solid form will be wax-like and may be molded into a predetermined shape or cast into a wide-mouthed container or mechanical dispensing device. To carry-out the invention, a user transfers a selected product to a portion of one's skin or other surface. One or more additional scented products are selected and applied in the same manner. The products are then manually mixed together on the skin or other surface to form a custom fragrance in-situ.

11 Claims, No Drawings

METHOD OF CREATING FRAGRANCES IN SITU

This application is a continuation of application Ser. No. 08/139570, filed Oct. 21, 1993, abandoned.

BACKGROUND OF THE INVENTION

1. Field of the Invention

The present invention pertains to the creation of customized fragrances. More particularly, the invention concerns the application of basic solid or semi-solid form scents upon one's skin or other surface to achieve a desired fragrance.

2. Description of Related Art

Although the number of different fragrances available to the public is almost unlimited, due to cost considerations, most individuals usually have no more than three or four different bottles of fragrances. As a result, one is oftentimes without the specific perfume, cologne or powder that will fit a particular mood or occasion.

In order to accommodate the above deficiency, a fragrance making kit was developed as shown in U. S. Pat. No. 2,822,082. This kit includes various raw materials, measuring means, mixing devices and instructions on using the above to compound perfumes, colognes, toilet waters and the like. The raw materials comprise essential oils, aromatic compounds, solvents and other chemicals considered necessary to produce the desired fragrance.

While the above kit permitted a user to produce a variety of scents for personal use, it obviously is not something one would do in preparation for an evening out. In fact, even with complete instructions, formulations involving multiple ingredients and careful calibrations are too cumbersome and time consuming for the average user to produce.

Additionally, the above process is wasteful. Liquid spillage is not uncommon. And, even when mixing the smallest quantities feasible, the final product will be at least one half ounce of liquid. Clearly, this is more than enough for several applications. But, what if the resultant fragrance did not turnout the way it was anticipated? Or, what if a mistake was made? Or, what if the desired fragrance was suitable for just a single special occasion? Obviously, any one of the above will result in the loss of costly materials.

Furthermore, it is known that liquid fragrances age and become concentrated over time by evaporation of the base. This, of course, alters the character of the fragrance.

Also, liquid fragrances smell different after a period of time on one's skin. And, once on the skin, they are hard to remove because they impregnate and spread over the skin very quickly.

Still further, liquid perfumes cannot be readily mixed upon one's skin. This is because the liquid carrier is oftentimes highly volatile and evaporates too quickly for effective and consistent mixing. In cases where the vehicles do not evaporate as quickly, e.g. oil and solvent bases, the aroma components still immediately diffuse into and over the skin. Thus, successive applications of different scents simply result in one scent overlying and masking another scent.

SUMMARY OF THE INVENTION

The present invention overcomes the above problems and provides a unique means for creating a custom fragrance directly upon one's skin. It provides a plurality of basic scents, each one of which is incorporated into a solid or semi-solid vehicle or carrier. As so formulated, each scented product can be molded into a predetermined shape for ease of use. Alternatively, the products can be utilized in conjunction with an individual dispensing means. Either way, one simply applies varying amounts of selected products to the skin or other surface and mixes them together to produce a custom fragrance in-situ.

The vehicles of the invention may be wax-like, gel-like or they may be in the form of a pressed powder. They do not include highly volatile materials. As such, effective transfer and/or mixing can occur with simple implements or with one's fingers. If the created fragrance is unappealing, it can be readily wiped-off or washed away.

Another advantage of the invention is that it allows just about anyone to create an infinite number of complex fragrances. This is accomplished by providing a custom fragrance-making set comprising separate containment means. Each containment means will house a scented product. The products are miscible with each other and the scents are compatible in regard to their ability to mix and produce a pleasing fragrance. For example, a set of basic floral scents may be provided wherein a touch of rose or jasmine product and a small amount of violet product can all be mixed together on the skin to develop a more complex, but very pleasant floral bouquet.

Furthermore, by varying the amount of each of the above components, one can create additional subtle variations of the original bouquet. Still further, floral scents can be used to modify other basic fragrances found in any one of the major categories. For example, a rose scent can be used in conjunction with an oriental or a green fragrance to produce an entirely different variety of fragrance. Thus, to carry out the objectives of the present invention, one needs only to have a wish to create a fragrance that satisfies their own personal olfactory senses. No particular skill or knowledge of perfumery is required.

DESCRIPTION OF THE PREFERRED EMBODIMENTS

In the fragrance industry, there are eight major classes of fragrances. These classes are referred to as Aldehydic, Chypre, Citrus, Floral, Fougere, Green, Oriental and Tobacco/Leather. Within each major classification, there are numerous balanced basic fragrance entities called accords. Thus, as used in this invention, the terms "basic scent", "base fragrance" or "scented product" will generally reference an accord.

For purposes of the invention, and out of respect to commercial reality, it is desirable to limit the number of basic scents to those that are most popular and which can be considered complete representations of a known scent on their own merit. In this way, a knowledge of perfumery is not required. Also, since each scent is of a finished product quality, it can be used "as is" whenever one wishes to wear a single fragrance.

With the above in mind, the invention comprehends the selection of at least three basic scents which will be compatible and produce pleasing fragrances when combined. Each selected scent is incorporated into a solid or semi-solid vehicle at a predetermined concentration. The mixture produces a scented product which is then molded into predetermined solid shapes. Most commonly, the product is placed into containment means such as open-mouthed containers, jars, vessels or collapsible tubes. An example of an open-mouthed container with a resealable closure is shown in U.S. Pat. No. 3,470,930.

Alternatively, the product may be molded into a form suitable for dispensing from the housing of a mechanical dispensing means. U.S. Pat. No. 2,753,991 is illustrative of the above wherein a molten solid form of the product is poured into a mold and base container. The product is cooled and both the container and product are then placed into a lipstick or lip balm type of dispensing device. The typical device has an outer housing enclosed by a cap. Upon actuation, internal mechanical means lift the product from the housing for application to one's skin in a manner well known in the art.

A user selects one of the aforementioned scented products, removes it from its container and applies it to a portion of the skin. Another scented product is removed from another container and applied adjacent to, or directly upon, the first scented product. The two products are then manually mixed together. Alternatively, one could apply one or more products to one wrist and one or more products to the opposing wrist or another part of the body. The product mixing step may then occur by rubbing the wrists together or rubbing one wrist against whatever other part of the body upon which the additional product was previously applied.

The foregoing steps may be repeated with different scented products. Also, the amount of each product can be varied per application or repeated applications of the same product can be made to produce the desired effect.

The semi-solid product forms of the invention will have a viscosity of about 25,000 cps and above. Such forms may be characterized as a thick cream, gel or ointment. Solid product forms, however, are not measurable with a viscosimeter. In such cases, a penetrometer may be used. However, penetrometer readings still do not provide a true portrayal of the desired solid form physical characteristics which are preferred to carry-out the method of this invention.

A criterion which is helpful is the ability of the solid form to yield a desired amount of the product when stroked with the finger at normal room temperature (60°–80° F.). Therefore, "yield" relates to the amount of product that will be displaced onto one's finger, or upon a similar acting implement means, when the finger/implement is moved across the product surface. It will be appreciated that exactness in measuring the quantities of product being used is not essential to carry-out the invention. Generally, however, the solid form should permit a user to remove from 0.01 to 0.10 gram product per stroke.

With the aforesaid quantity of product being transferred, it is preferred that the product have a fragrance concentration of from 5% to 60% by weight. Within this range, a single stroke of solid product will roughly equal a single application of liquid fragrance which has a similar concentration of fragrance.

For purposes of the present invention, the term "solid" shall reference a rigid material that has structural integrity but is wax-like or has the characteristics of pressed powder. The term "semi-solid" refers to a non-rigid material that has no structural integrity but is very viscous and gel-like and must be housed in a containment means such as a collapsible tube or an open-mouthed vessel.

Product Formulations

The following are examples of solid and semi-solid product formulations which are used to carry-out the invention. In general, the basic compositions will comprise 20–80 wt % vehicle and 5–60 wt % base fragrance. Binders and/or lubricants in the amounts of 0.5–15 wt % may also be added. The binders and lubricants may comprise any one or combination of, zinc stearate, mineral oil, lanolin alcohols and fatty acid esters.

The base fragrances referenced below comprise liquids. However, they could also comprehend powders or crystals. As used in the following formulations, the term "base fragrance" is intended to encompass all of the above.

EXAMPLE I

|  | % |
| --- | --- |
| Base Fragrance | 15.00 |
| Beeswax | 28.00 |
| Sweet Almond Oil | 57.00 |

EXAMPLE II

|  | % |
| --- | --- |
| Base Fragrance | 20.00 |
| Beeswax | 28.00 |
| Sweet Almond Oil | 52.00 |

EXAMPLE III

|  | % |
| --- | --- |
| Base Fragrance | 50.00 |
| Beeswax | 42.00 |
| Sweet Almond Oil | 8.00 |

EXAMPLE IV

|  | % |
| --- | --- |
| Base Fragrance | 30.00 |
| Beeswax (synthetic) | 28.00 |
| Sweet Almond Oil | 21.00 |
| Kukui Nut Oil | 20.00 |
| Silica | 1.00 |

EXAMPLE V

|  | % |
| --- | --- |
| Petrolatum | 20.00 |
| Isopropyl Myristate | 24.00 |
| Aluminum Hydrate | 12.00 |
| Ozokerite | 9.00 |
| Beeswax | 5.00 |
| Myristyl Alcohol | 13.00 |
| Base Fragrance | 17.00 |

EXAMPLE VI

|  | % |
| --- | --- |
| Hydrogenated Coconut Oil | 41.00 |
| Petrolatum | 10.00 |
| Acetylated Monoglycerides | 10.00 |
| Microcrystalline Wax | 14.00 |
| Ceresin | 5.00 |
| Silica | 2.00 |
| Base Fragrance | 18.00 |

EXAMPLE VII

|  | % |
| --- | --- |
| Isopropyl Palmitate | 49.95 |
| Ceresin | 23.00 |
| Beeswax | 15.00 |
| Butylparaban | 0.05 |
| Base Fragrance | 12.00 |

Products from the above Examples are made by mixing and melting all of the ingredients until they are homogeneous, then cooling to about 60°–65° C. and adding the selected base fragrance. The mixture is then poured into molds or other containment means depending on the physical form of the final product being produced. The mixture is then allowed to cool to ambient temperature.

EXAMPLE VIII

|  | % |  | % |
| --- | --- | --- | --- |
| Water | 80.11 | Dioctyl Adipate | 2.00 |
| Triethanolamine | 0.70 | Stearic Acid | 7.50 |
| Methylparaben | 0.15 | PPG 30 Cetyl Ether | 2.00 |
| Polysorbate 20 | 0.15 | Propylparaben | 0.05 |
| Carbomer | 0.30 | BHA | 0.03 |
| Pentasodium Pentetate | 0.01 | Base Fragrance | 7.00 |

A scented product is produced from the above formulation as follows:

A. Heat water to 80° C. and dust in Carbomer and Methylparaben with high speed mixing. Add Pentasodium Pentetate, Polysorbate 20 and Triethanolamine.

B. Heat Dioctyl Adipate, Stearate Acid, PPG 30 Cetyl Ether, Propylparaben and BHA to 80° C.

C. Add B to A with mixing and cool to 55° C. Mix in base fragrance, pour into a mold and cool to ambient temperature.

EXAMPLE IX

|  | % |  | % |
| --- | --- | --- | --- |
| Water | 66.71 | EDTA Sodium | 0.04 |
| Propylene Glycol | 5.00 | Cetyl Alcohol | 5.00 |
| Sodium Lauryl Sulfate | 2.00 | Stearyl Alcohol | 6.00 |
| Methylparaben | 0.15 | Spermaceti | 5.00 |
| Propylparaben | 0.10 | Base Fragrance | 10.00 |

A scented product is produced from the above formulation in the following manner:

Heat water to 80° C. add propylene glycol, methylparaben, propylparaben, EDTA sodium and sodium lauryl sulfate with slow mixing.

Melt cetyl alcohol, stearyl alcohol and spermaceti in a separate vessel to 75° C.

Add the oil phase to the water phase with constant slow mixing and cool to 50° C. Mix-in the base fragrance at 50° C. pour into a containment means and then cool to ambient temperature.

It will be appreciated that the invention also comprehends the use of pressed powder formulations to produce the aforementioned solid form product. In such cases, the base fragrances may be encapsulated, adsorbed, absorbed or entrapped by particulate carriers. Examples of useful carriers are polymer beads, powders of talc, kaolin and starch and crystals of silica and calcium carbonate. The above may be used alone or in combination with each other.

Examples of a pressed powder form of the invention are as follows:

EXAMPLE X

|  | % |
| --- | --- |
| Zinc Stearate | 78.45 |
| Mineral Oil 65/75 | 3.00 |
| Lanolin Alcohol | 0.50 |
| Talc | 3.00 |
| Entrapped Base Fragrance Powder | 15.00 |
| Butylparaben | 0.05 |

The above ingredients are combined to form a rigid pressed powder product in the following manner:

A. Heat Zinc Stearate, Mineral Oil 65/75 and Lanolin Alcohol together until homogeneous.

B. Mix talc and entrapped fragrance powder in a suitable powder mixer.

C. Spray "A" into the mixer containing "B".

D. Compress into the desired shape.

EXAMPLE XI

|  | % |
| --- | --- |
| Magnesium Stearate | 5.0 |
| Calcium Carbonate | 10.00 |
| Base Fragrance | 15.00 |
| Talc | 68.00 |
| Colloidal Magnesium Aluminum Silicate (5%) in Water | 2.00 |

Mix base fragrance with calcium carbonate in a ribbon blender or a "V" blender. Add the magnesium stearate and talc until the mixture is homogeneous. Spray in the CMAS 5% binder and mix until it is properly dispersed. Color and preservative may be added.

An example of a powder fragrance in an entrapped polymer is as follows:

EXAMPLE XII

|  | % |
| --- | --- |
| Magnesium Stearate | 5.00 |
| Acrylates Copolymer (Polytrap ®) | 7.00 |
| Fragrance | 20.00 |
| Talc | 66.50 |
| Colloidal Magnesium Aluminum Silicate (5%) in Water | 1.50 |

Mix fragrance with Polytrap® and then proceed as in Example XI.

Method Of Using The Scented Products

To create a new fragrance from a given set of basic scents, a user will remove a small amount of product from the aforementioned product form with a finger or a suitable transfer implement. The removed product is then placed upon a selected surface. The amount of product applied can be measured to some extent by visual observation or by the characteristics of the implement means being used and by the number of times this step is repeated.

Subsequently, a selected quantity of another scented product is transferred from its product form and applied to a predetermined surface, i.e., a portion of one's skin, clothing or accouterments. Thereafter, the products are mixed together on the surface. Again, this step can be accomplished manually with one's finger, or with an implement, or with a mechanical dispensing means.

It is preferred that clean fingers and implements be used. This will serve to prevent contamination of one scented product with another. Examples of implement means useful with the invention are rigid sticks such as plastic sticks with a flat end or flat wooden sticks. Other examples would be utensils, fibrous-tipped swabs or wands of varying sizes and puffs for powders. As a convenience, it is expected that multiple disposable implements could be provided with each set of fragrances.

Examples of mechanical dispensing means suitable for use with the invention are rotary or push-up devices typically used with lipsticks, glue sticks and lip balms. An example of a mechanical device useful with the invention is shown in U.S. Pat. No. 2,309,000 which is herein incorporated by reference.

With the above devices, a solid state product is elevated from within a housing to expose incremental portions of the product. As so exposed, a user may apply the product by rubbing the exposed portion against a selected surface. When using mechanical devices, it is best not to apply the second and subsequent scented products directly upon each other. Otherwise, contamination may occur.

The following are illustrative examples of the above-described methods:

EXAMPLE XIII

A set of five containers are provided with each container holding a basic scent product in the floral fragrance category. The products are produced in accordance with Example I and have a solid physical character. Each container holds a different scent comprising violet, muguet, rose, hyacinth and gardenia. A small flat implement is used to remove approximately 0.05 gram of muguet product from the container. This product is deposited upon the underside of one's wrist. The above step is repeated with a clean finger or implement whereby 0.08 gram of violet product is rubbed directly into the previously applied muguet product. The resultant fragrance provides a nuance of violet with a lily undertone.

EXAMPLE XIV

A set of five lip balm type of rotary mechanical dispensing containers are provided having solid forms of the same fragrance products of Example XIII. In this case, the container cap will be removed and the exposed solid stick product form is rubbed directly upon one's wrist. This procedure will dislodge about 0.04 gram of product per swipe across the skin. To produce the sweet bouquet of a flower, a user makes two strokes across the skin with the gardenia product. This step is followed by two swipes of hyacinth product and then two swipes of rose product. The application of each different scent are made upon adjacent parts of one's skin. Thereafter, the products are manually mixed together with a finger to produce the in-situ flower bouquet.

EXAMPLE XV

A set of six collapsible tubes are provided with each tube containing a semi-solid product form of an accord comprising amber, woody, leather, mossy, animal and green.

In this case, similar amounts of animal, woody and floral accords are squeezed from each respective tube onto adjacent areas of the skin and mixed together. The resultant mixture provides an enchanting musk scent with floral top notes.

EXAMPLE XVI

A set of five compressed powder forms are provided in separate containers with each form containing a citrus, floral, woody and green accord. Like portions of each powder form are transferred to a selected body area by rubbing the form against the skin or with one's finger, puff or other implement. The resultant fragrance has a floral bouquet with fruity notes and a woody undertone.

It can be seen that any of the physical forms described in this invention can be applied to a body area or other surface which then may be used as a mixing and blending site. For example, in addition to one's neck, ear, ankle or wrist, combinations of scented products can be applied to predetermined parts of a necklace, handkerchief, scarf, bracelet or the like.

Note the following example:

EXAMPLE XVII

A portion of a mossy accord gel is removed from a jar or tube and applied to the palm of the hand. Another portion of a green accord gel is placed adjacent to the first mossy accord. Finally, a spicy accord is placed adjacent to the first two applications. The three accords are then blended together in the palm and transferred to an accouterment such as a cloth or article of jewelry. Alternatively, the mixture can be transferred by rubbing the fingers and palms over other parts of the body.

If one wishes to make a larger quantity of a preferred fragrance, the following procedure may be used: The desired amounts of each solid or semi-solid product is measured and then divided into segments. The segments are combined in a pan and then mixed together under low heat. The warm flowable product is then poured into a dispensing containment means or back into an empty one of the original containers where cooling to ambient temperature occurs. In this way the desired custom fragrance is premade and can be dispensed from a singular source.

While the foregoing descriptions and examples describe specific details of the invention, it will be apparent to those skilled in the art that variations, alterations, and/or modifications may be made without departing from the spirit and scope of the invention. Accordingly, the invention is not to be limited by the above specific disclosures, but only by the scope of the appended claims.

I claim:

1. The method of producing a custom fragrance directly upon one's skin comprising the steps of:

A. selecting at least two scents:

B. mixing each selected scent with a nonvolatile vehicle having a physical state selected from the group consisting of a gel, wax and pressed powder to produce at least two coresponding scented products;

C. placing each scented product within a respective separate containment means;

D. applying a first one of said scented products to said skin;

E. applying a second one of said scented products to said skin; and,

F. mixing together said first one and said second one of said scented products while on said skin to create a custom fragrance.

2. The method of claim 1 wherein at least steps D, E and F are carried-out manually with one's finger.

3. The method of claim 1 wherein at least steps D, E and F are carried-out manually with an implement means selected from the group consisting of rigid stick, utensil, puff and fibrous-tipped swab.

4. The method of claim 1 wherein said containment means comprises an open-mouthed container and at least steps D and E are carried out by stroking a respective scented product with a means selected from the group consisting of one's finger and an implement means.

5. The method of claim 4 wherein 0.01 to 0.10 gram of scented product are removed per stroke.

6. The method of claim 1 wherein each scented product is in a gel physical state and said containment means comprises a collapsible tube whereby steps D and E are carried-out by squeezing said tube and dispensing scented product upon said skin.

7. The method of claim 1 wherein each scented product is in a pressed-powder physical state and at least steps D and E are carried-out by rubbing the scented product across said skin.

8. The method of claim 1 wherein each scented product is in a wax physical state and said containment means comprises a housing with a dispensing means selected from the group consisting of a rotary assembly and a push-up assembly whereby steps D and E are carried-out by elevating a portion of a scented product out of each respective housing and rubbing said elevated portion across said skin.

9. The method of claim 1 wherein each scented product comprises 5–60 wt % base fragrance and 20–80 wt % vehicle selected from the group consisting of petrolatum, vegetable oil, wax, clay and powder.

10. The method of claim 9 wherein each scented product includes a member selected from the group consisting of any one or combination of 0.5–15 wt % binder and 0.5–15 wt % lubricant.

11. The method of claim 10 wherein said binder and lubricant are selected from the group consisting of any one or combination of zinc stearate, mineral oil, lanolin, alcohols and fatty acid esters.

* * * * *

(12) REEXAMINATION CERTIFICATE (4364th)
United States Patent
Saute

(10) Number: US 5,626,155 C1
(45) Certificate Issued: May 22, 2001

(54) METHOD OF CREATING FRAGRANCES IN SITU

(75) Inventor: Robert E. Saute, 10236 Mossy Rock Cir., Los Angeles, CA (US) 90077

(73) Assignee: Robert E. Saute, Los Angeles, CA (US)

Reexamination Request:
No. 90/005,262, Feb. 17, 1999

Reexamination Certificate for:
Patent No.: 5,626,155
Issued: May 6, 1997
Appl. No.: 08/391,727
Filed: Feb. 21, 1995

Related U.S. Application Data

(63) Continuation of application No. 08/139,570, filed on Oct. 21, 1993, now abandoned.

(51) Int. Cl.$^7$ ..................................................... A45D 34/00
(52) U.S. Cl. ......................... 132/200; 434/377; 132/320
(58) Field of Search ............................. 434/377; 132/200, 132/320, 286, 294, 297, 317, 318; 206/232, 581, 823; 512/4; 422/4, 5

(56) References Cited

U.S. PATENT DOCUMENTS

| | | | |
|---|---|---|---|
| 4,067,824 | * | 1/1978 | Teng et al. . |
| 4,226,889 | * | 10/1980 | Yuhas . |
| 4,368,187 | * | 1/1983 | Flom et al. . |
| 4,617,147 | * | 10/1986 | Shibanai . |
| 4,778,783 | * | 10/1988 | Gondra et al. . |
| 5,120,709 | * | 6/1992 | Cella et al. . |
| 5,223,251 | * | 6/1993 | Nuchols . |

OTHER PUBLICATIONS

Tisserand, "The Art of Aromatheraphy", Healing Art Press, pp 143–159, 1997.*
Poucher, "Perfumes, Cosmetics and Soaps", vol. II, 7th Ed., Chapman and Hall Ltd, pp 3–20, 415–422, 1959.*
Flick, "Cosmetic and Toiletry Formulations", vol. I, 2nd Ed., Noyes Publications, pp 327–333, 1989.*
Keithler, "The Formulation of Cosmetic and Cosmetic Specialities", Drug & Cosmetic Industry, pp 423–432, 1956.*

* cited by examiner

*Primary Examiner*—Todd E. Manahan

(57) ABSTRACT

A method of producing a custom fragrance is provided comprising the steps of selecting a series of basic scents. The scents are incorporated into a semi-solid or solid vehicle to produce a scented product. With the semi-solid vehicle the product will be in the form of a viscous cream, gel or ointment contained in a squeeze tube, jar or the like. The solid form will be wax-like and may be molded into a predetermined shape or cast into a wide-mouthed container or mechanical dispensing device. To carry-out the invention, a user transfers a selected product to a portion of one's skin or other surface. One or more additional scented products are selected and applied in the same manner. The products are then manually mixed together on the skin or other surface to form a custom fragrance in-situ.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–11, dependent on an amended claim, are determined to be patentable.

1. The method of producing a custom fragrance directly upon one's skin comprising the steps of:
   A. selecting at least two *basic* scents[:];
   B. mixing each selected *basic* scent with a [nonvolatile] *non-volatile* vehicle having a *solid or semi-solid* physical state selected from the group consisting of a gel, wax and pressed powder to produce at least two corresponding scented products;
   C. placing each scented product within a respective separate containment means;
   D. applying a first one of said scented products to said skin;
   E. applying a second one of said scented products to said skin; and,
   F. *manually* mixing together said first one and said second one of said scented products while on said skin to create a custom fragrance.

\* \* \* \* \*